US00PP31442P2

(12) United States Plant Patent
Kordes

(10) Patent No.: US PP31,442 P2
(45) Date of Patent: Feb. 18, 2020

(54) MINIATURE ROSE PLANT NAMED 'KORONE005'

(50) Latin Name: *Rosa hybrida*
Varietal Denomination: KORone005

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/998,223

(22) Filed: Jul. 19, 2018

(30) Foreign Application Priority Data

May 28, 2018 (QZ) ..... PBR 2018/1392

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./121, 128, 148
CPC ..... A01H 5/0222; A01H 5/02; A01H 5/00; A01H 6/74; A01H 6/749
See application file for complete search history.

(56) References Cited

U.S. PATENT DOCUMENTS

PP25,004 P2 10/2014 Kordes

*Primary Examiner* — June Hwu
(74) *Attorney, Agent, or Firm* — Buchanan Ingersoll & Rooney PC

(57) ABSTRACT

A new and distinct variety of Miniature Rose Plant, herein referred to by its cultivar name, 'KORone005', is provided which forms attractive, double, pink colored blossoms. The vegetation is vigorous and the growth habit is upright. Attractive ornamental foliage is formed. The new variety is particularly well suited for providing distinctive ornamentation in the landscape.

1 Drawing Sheet

Botanical/commercial classification:
Latin name.—*Rosa hybrida.*
Common name—Miniature Rose Plant.
Varietal denomination: 'KORone005'.

CROSS-REFERENCE TO RELATED APPLICATIONS

This application claims priority to Plant Breeders' Right Application Number 2018/1392, which was filed at Community Plant Variety Office in the European Union on May 28, 2018, the contents of which are hereby incorporated by reference for all purposes.

SUMMARY OF THE INVENTION

The new variety of *Rosa hybrida* Miniature Rose Plant of the present invention was created during 2014 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling (non-patented in the United States). The male parent (i.e., pollen parent) of the new variety was the 'KORpot028' variety (U.S. Plant Pat. No. 25,004).

The parentage can be summarized as follows:

unnamed seedling x 'KORpot028'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) forms attractive, double, pink colored blossoms,
(b) exhibits an upright growth habit,
(c) forms vigorous vegetation, and
(d) forms attractive ornamental foliage.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling seed parent exhibits white colored flowers, a medium and bushy growth habit, and smaller flowers compared to the pink colored flowers of the new variety, which exhibits an upright growth habit. Additionally, the 'KORpot028' variety (i.e., pollen parent) exhibits dark red colored flowers and an upright and bushy growth habit, whereas the new variety displays double, pink colored flowers and an upright growth habit; additionally, the new variety exhibits larger flowers compared to the 'KORpot028' variety. Moreover, the new variety can be readily distinguished from non-parental related similar varieties. For example, the 'First Prize' variety (U.S. Plant Pat. No. 2,774) exhibits larger diameter flowers with lower number of petals and less globular shaped buds compared to the new variety.

The new variety has been found to undergo asexual propagation in Klein Offenseth-Sparrieshoop, Germany by a number of routes such as vegetative cuttings, typically internodal one node cuttings. Asexual propagation techniques in Germany, such as vegetative cuttings, typically internodal one node cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORone005'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in 6.0 cm containers.

FIG. 1—illustrates a specimen of a blossom.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during February, while growing in a one-gallon container on its own roots in a greenhouse at Cochranville, Pa.

Class: Miniature Rose Plant.

Plant:

*Habit*.—Very upright.

*Height*.—Approximately 50.0 cm on average.

*Width*.—Approximately 30.0 cm on average.

Branches:

*Immature stem color*.—Commonly near Yellow-Green Group 144A.

*Mature stem color*.—Commonly near Greyed-Orange Group 165A.

*Main stem length*.—Approximately 50.0 cm on average.

*Secondary stem length*.—Approximately 20.0 cm on average.

*Surface texture*.—Immature stems: glabrous. Mature stems: smooth to rough where the wood is becoming harder.

*Thorns*.—Young thorns: moderate amount; length is approximately 5.0 mm on average, width is approximately 4.0 mm at point of attachment on average, and color is commonly near Greyed-Orange Group 177A. Old thorns: moderate amount; length is approximately 5.0 mm on average, width is approximately 1.0 mm at point of attachment on average, and color is commonly near Greyed-Orange Group 176B.

Foliage:

*General appearance*.—Ornamental.

*Young foliage*.—Upper surface color: commonly near Yellow-Green Group 144A. Under surface color: commonly near Yellow-Green Group 147C with Greyed-Purple Group 184B at margins.

*Old foliage*.—Upper surface color: commonly near Green Group 136A with midvein venation of near Greyed-Red Group 178A and near Green Group 136B for all other veins. Under surface color: commonly near Green Group 138A with venation of near Green Group 138B.

*Petioles*.—Upper surface: texture is smooth, color is commonly near Yellow-Green Group 144B and near Yellow-Green Group 144A towards the stipules. Under surface: texture is mostly smooth with sparse prickles, color is commonly near Yellow-Green Group 144B.

*Rachis*.—Color: upper surface is commonly near Greyed-Red Group 178B, under surface is commonly near Yellow-Green Group 146D.

*Stipules*.—Length: approximately 1.2 cm on average. Width: approximately 4.0 mm on average. Margin: entire to erose. Color: upper surface is commonly near Yellow-Green Group 144B; under surface is commonly near Yellow-Green Group 144D.

*Leaf margin*.—Serrate.

Leaflets:

*Number*.—3, 5, and 7.

*Arrangement*.—Odd pinnate.

*Shape*.—Ovate; apex is acute; and base is rounded.

*Venation*.—Pattern is reticulate.

*Texture*.—Upper surface is smooth; lower surface is smooth.

*Margin undulation*.—Absent.

*Glossiness*.—Upper side of leaf is semi-glossy.

*Size*.—Terminal leaflet: length is approximately 5.5 cm on average and width is approximately 3.5 cm on average. Lower leaflets: length is approximately 4.3 cm on average and width is approximately 2.7 cm on average. 5-leaflet leaf: length is approximately 12.0 cm on average and width is approximately 8.5 cm on average.

Inflorescence:

*Number of flowers*.—Approximately 1 on a young plant at once and up to 4 on an older plant at once.

*Number of blooms per stem*.—Commonly 1 bloom per stem on average.

*Peduncle*.—Color: commonly Yellow-Green Group N144D. Diameter: approximately 1.0 cm on average. Length: approximately 1.0 cm on average. Surface texture: glabrous. Strength: strong.

*Sepals*.—Number: commonly 5. Upper surface color and texture: covered in short pubescence and color is commonly near Yellow-Green Group 144A. Under surface color and texture: puberulent and color is commonly near Yellow-Green Group 144A. Size: length is approximately 2.5 cm on average and width is approximately 1.5 mm on average. Shape: lanceolate; apex is acute to aristate; base is truncate to flat as it joins the receptacle. Margin: entire with occasional extensions on two or three sepals measuring approximately 7.0 mm in length and approximately 1.0 mm in width.

*Bud*.—Shape: globular. Size: length is approximately 1.5 cm on average; width is approximately 1.0 cm on average. Color (when opening): commonly a blend of near Orange-Red Group 34C and Yellow Group 11A.

*Flower*.—Double, pink colored. Form: double, cuplike. Profile: convex, becoming flatter as it fully opens. Diameter: approximately 6.5 cm on average. Height: approximately 4.0 cm on average. Duration: commonly on the plant approximately 35 days on average. Petal color when first and fully open: upper surface is commonly near Red-Purple Group 65B with a slight basal spot of near Yellow Group 11D; under surface is commonly near Red-Purple Group 65C with a slight basal spot of near White Group NN155A. Petal color when fading: upper surface is commonly near Red-Purple Group 65D with a slight basal spot of near White Group N155C and under surface is commonly near Red-Purple Group 69D. Basal spot size on upper petal surface: small.

*Fragrance*.—Light sweet fragrance.

*Petal*.—Number: approximately 94 on average. Drop: average. Length: inner petals are approximately 2.5 cm on average and outer petals are approximately 3.5 cm on average. Width: inner petals are approximately 1.7 cm on average and outer petals are approximately 3.0 cm on average. Shape: overall shape is broadly obovate; apex is round; and base is cuneate. Texture: upper and under surface is glabrous. Margin: entire.

*Petaloids*.—Number: approximately 10 per flower on average. Color: upper and under surfaces are commonly near Red-Purple Group 65C. Size: length is approximately 1.4 cm on average and width is approximately 6.0 mm on average. Texture: smooth. Margins: variable, entire to erose. Shape: variable, oblong and mostly curving inward; apex is round, and base is cuneate.

*Stamen*.—Number: approximately 80 on average. Anthers: number is about 80 and color is commonly near Greyed-Orange Group 165D. Filaments: length is approximately 4.0 mm on average and color is commonly near Yellow Group 4D.

*Pistils*.—Arrangement: separate and free. Number: approximately 80 on average. Style: color is mostly near Yellow-Green Group 149D and length is approximately 1.0 mm on average. Stigma: color is commonly near Yellow-Orange Group 17D, diameter is typically less than 1.0 mm, and shape is fan shaped.

*Ovary*.—Length is approximately 3.0 mm, width is approximately 1.0 mm, and color is commonly near White Group 155D.

*Receptacle*.—The underdeveloped achenes attach along the inside bottom and side walls of the receptacle; diameter is approximately 1.0 cm on average, shape is round, color is commonly near Yellow-Green Group 144A, and surface texture is smooth.

*Pollen*.—None observed.

*Hips/seed*.—None observed.

Development:

*Vegetation*.—Dark green, vigorous, and strong.

*Blooming*.—Produces few large individual blooms at a given time and will rebloom again in the same season; typical months of blooming season is year round if grown in a greenhouse.

*Winter hardiness/hardiness zone*.—Unknown.

*Resistance to disease*.—Good resistance to *Botrytis* (*Botrytis cinerea*) disease under normal greenhouse growing conditions in Cochranville, Pa.

Plants of the 'KORone005' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) forms attractive, double, pink colored blossoms, (b) exhibits an upright growth habit, (c) forms vigorous vegetation, and (d) forms attractive ornamental foliage;

substantially as herein shown and described.

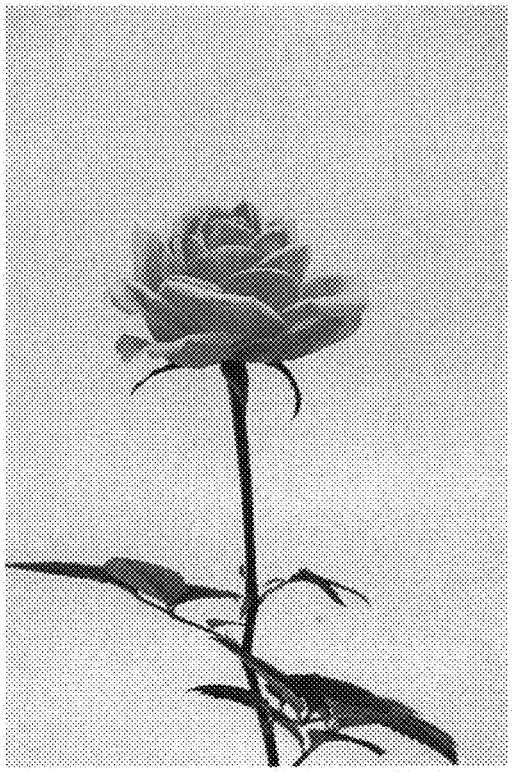

* * * * *